United States Patent [19]

Petersen

[11] 4,329,484

[45] May 11, 1982

[54] CONTINUOUS PROCESS FOR PREPARING ACYLOXYSILANES

[75] Inventor: Louis P. Petersen, Schenectady, N.Y.

[73] Assignee: General Electric Company, Waterford, N.Y.

[21] Appl. No.: 278,542

[22] Filed: Jun. 29, 1981

[51] Int. Cl.$^3$ .............................. C07F 7/04; C07F 7/08
[52] U.S. Cl. ..................................................... 556/442
[58] Field of Search ......................................... 556/442

[56] References Cited

U.S. PATENT DOCUMENTS

| | | | |
|---|---|---|---|
| 2,017,000 | 8/1935 | Hintermaier | 556/442 X |
| 2,405,988 | 8/1946 | Barry | 556/442 |
| 2,537,073 | 1/1951 | Mackenzie et al. | 260/448.8 |
| 2,566,347 | 9/1951 | Mackenzie | 556/442 |
| 2,866,800 | 12/1958 | Mackenzie et al. | 556/442 |
| 3,700,714 | 10/1972 | Hamilton et al. | 260/448.2 B |
| 3,701,753 | 10/1972 | Shaw | 260/9 R |
| 3,792,071 | 2/1974 | Nitzsche et al. | 260/448.8 R |
| 3,974,198 | 8/1976 | Ashby | 260/448.2 E |
| 4,028,391 | 6/1977 | Foley | 260/448.2 D |
| 4,176,130 | 11/1979 | John et al. | 260/448.2 E |

FOREIGN PATENT DOCUMENTS 2801780  7/1979  Fed. Rep. of Germany ...... 556/442 UX

*Primary Examiner*—Paul F. Shaver

[57] ABSTRACT

Acyloxysilanes are prepared by reacting a chlorosilane with an aliphatic carboxylic acid in a column at an elevated temperature and preferably at a pressure of about 760 mm Hg. wherein the aliphatic carboxylic acid in the vapor phase passes upward from the bottom of the column countercurrent to the flow of the chlorosilane passing downward in the column. The improvement comprises introducing the carboxylic acid into the column at such a rate that the carboxylic acid exceeds 1.3 moles per gram atom of silicon-bonded chlorine in the column and removing low boiling reaction by-products from the top of the column while collecting the acyloxysilane product dissolved in the aliphatic carboxylic acid at the bottom of the column. In a preferred embodiment, methyltriacetoxysilane is prepared by reacting methyltrichlorosilane with acetic acid in a heated fractionation column.

18 Claims, No Drawings

CONTINUOUS PROCESS FOR PREPARING ACYLOXYSILANES

BACKGROUND OF THE INVENTION

The present invention relates to a process for producing acyloxysilanes, and more particularly, to an improved process for the continuous production of acyloxysilanes in a system which substantially increases capacity over prior art systems.

Acyloxysilanes are well known cross-linking agents for 1-part room temperature vulcanizable silicone rubber compositions. One common acyloxysilane cross-linking agent is methyltriacetoxysilane.

Acyloxysilane cross-linking agent has been made by the reaction of an appropriate chlorosilane with a carboxylic anhydride or with a carboxylic acid. One process for preparing acyloxysilanes by reacting a chlorosilane with a carboxylic acid or carboxylic acid anhydride in the presence of an iron complexing agent is disclosed in U.S. Pat. No. 3,974,198. In U.S. Pat. No. 3,974,198, an aliphatic carboxylic acid, such as, glacial acetic acid, was added at the top of a distilling column to a refluxing mixture of a chlorosilane in an organic solvent, such as hexane, containing an iron complexing agent. After the completion of the addition of the aliphatic carboxylic acid, the solvent was removed by distillation, and the acyloxysilane compound was eventually isolated from the mixture.

Aliphatic carboxylic acid in the vapor phase is passed upwards from the bottom of a column filled with Raschig rings countercurrent to a flow of chlorosilane in U.S. Pat. No. 4,176,130. However, in U.S. Pat. No. 4,176,130 only a limited amount of aliphatic carboxylic acid is introduced into the column so that the feed rate of the carboxylic acid does not exceed 1.3 moles per gram atom of silicon-bonded chlorine in the column. Thus, at most, only a very slight excess of aliphatic carboxylic acid is introduced into the column in U.S. Pat. No. 4,176,130. The liquid glacial acetic acid vaporizes as it enters the column, and the acetic acid vapor rises against the flow of the chlorosilane. In more preferred embodiments, U.S. Pat. No. 4,176,130 specifies operation of the column at 50 to 300 mm (Hg) absolute such that the product exiting from the reboiler is substantially free of acetic acid. The reduction of absolute pressure reduces the temperatures in the column, reduces the density of the vapor phase, and reduces the equilibrium concentration of the chlorosilane monomer (methyltrichlorosilane or ethyltrichlorosilane) in the liquid phase (primarily liquid acetic acid). Thus, operation at pressures substantially below atmospheric pressure reduces the rate of reaction due to lower temperature and lower concentration of chlorosilane reactant in the liquid phase in the column and reduces the rate of mass transfer of unreacted chlorosilane from the vapor phase to the liquid phase. In addition, the slight excess of carboxylic acid results in a lower reaction rate in contrast to an excess of about 30 to 100% above stoichiometric requirements. The practical use of acyloxysilanes produced by this method requires that the remaining unreacted chlorine attached to silicon be reduced to a level of at least 50 ppm. and preferably below 10 ppm. The process described in U.S. Pat. No. 4,176,130 reduces the rate of reaction to a level that seriously limits the column throughput if the product requirement of less than 50 ppm., and preferably less than 10 ppm. of residual chloride, is to be obtained. The formation of dimer at the bottom of the column is a significant side reaction that results from thermal decomposition of monomeric acyloxysilanes or from a reaction of the chlorosilane with acyloxysilane or both. The dimer is represented by the following formula:

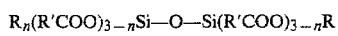

$$R_n(R'COO)_{3-n}Si-O-Si(R'COO)_{3-n}R$$

wherein R and R' are alkyl radicals generally of 1 to about 8 carbon atoms and n is 1 to 3. When the reactants form dimer, it reduces the amount of product. Thus, it is desirable to reduce the amount of dimer formed from the reaction, or to increase column throughput to provide commercial quantities of the acyloxysilanes even though the dimer is formed.

The continuous prior art processes are also disadvantageous insofar as low boiling contaminants generally accumulate in the column, and the low boiling contaminants reduce the column temperature. Accordingly, it is desirable to provide a process which eliminates this problem so that the column temperature can be maintained at a steady maximum temperature.

SUMMARY OF THE INVENTION

It is the primary object of the present invention to provide an improved process for producing acyloxysilanes by reacting a chlorosilane with an aliphatic carboxylic acid in a column at an elevated temperature.

It is another object of the present invention to provide an improved process for producing acyloxysilanes by reacting a chlorosilane with an aliphatic carboxylic acid in a column at elevated temperatures, wherein the aliphatic carboxylic acid in the vapor phase passes upward from the bottom of the column countercurrent to the flow of the chlorosilane passing downward in the column.

It is an additional object of the present invention to provide an improved process for producing acyloxysilanes in a system which maintains the column temperature at a steady maximum temperature.

Still another object of the present invention is to provide a process for producing acyloxysilanes by reacting a chlorosilane with an aliphatic carboxylic acid in a column at an elevated temperature and at substantially atmospheric pressure.

Another object of the present invention is to provide a process for producing acyloxysilanes by reacting a chlorosilane with an aliphatic carboxylic acid in a column at an elevated temperature wherein the column capacity is substantially increased.

It is another object of the present invention to provide a continuous process for producing acyloxysilanes having less than 50 ppm. residual chloride.

In accordance with the foregoing objects, there is provided a process for producing acyloxysilanes by reacting a chlorosilane with an aliphatic carboxylic acid in a column at an elevated temperature wherein the aliphatic carboxylic acid in the vapor phase passes upward from the bottom of the column countercurrent to the flow of the chlorosilane passing downward in the column, the improvement comprising introducing the carboxylic acid into the column at such a rate that the carboxylic acid exceeds 1.3 moles per gram atom of silicon-bonded chlorine in the column, and removing low boiling reaction by-products from the top of the column while collecting the acyloxysilane product at the bottom of the column.

The aliphatic carboxylic acid is in substantial excess of the chlorosilane reactant, that is, greater than 1.3 moles per gram atom of silicon-bonded chlorine, so that the aliphatic carboxylic acid acts as a solvent, and the reacting mixture becomes distributed throughout the column as a solution of the chlorosilane monomer in the aliphatic carboxylic acid. The product discharged from the lower end of the column is an aliphatic carboxylic acid solution of the acyloxysilane product. By the process of the present invention, column capacity is increased as much as about 14 to about 20 times that of the prior art processes. This increase in column capacity increases the efficiency of the process and results in substantial economy in the production of the acyloxysilanes.

Generally, the chlorosilanes which may be used in the process of the present invention, have the general formula:

$$R_nSiCl_{4-n}$$

wherein R is an alkyl radical having from 1 to about 8 carbon atoms, and n varies from 0 to 3. Other chlorosilanes which may be employed in the process of this invention are those having the general formula:

$$Cl_{3-b}SiR_bR'R_bSiCl_{3-b}$$

wherein R represents the same or different substituted or unsubstituted hydrocarbon radicals having from 1 to about 8 carbon atoms, R' represents a bivalent hydrocarbon radical, for example, an ethylene or phenylene radical, and b is 1 or 2.

DETAILED DESCRIPTION OF THE INVENTION

In the chlorosilanes having the formula:

$$R_nSiCl_{4-n}$$

for producing acyloxysilanes in accordance with the process of the present invention, R may be the same or different substituted and unsubstituted hydrocarbon radicals having from 1 to about 8 carbon atoms, and n may be 0, 1, 2 or 3. Examples of various specific hydrocarbon radicals and classes of hydrocarbon radicals represented by R in the formula above are alkyl radicals, such as methyl, ethyl, propyl, isopropyl, butyl, sec-butyl, octyl, and 2-ethylhexyl radicals; alkenyl radicals such as vinyl, and allyl radicals; the hexadienyl radicals; cycloalkyl radicals, such as cyclopentyl, cyclohexyl, and cycloheptyl radicals; cycloalkenyl radicals; aromatic hydrocarbon radicals, such as phenyl, and naphthyl radicals; aralkyl radicals, such as benzyl and phenylethyl radicals; alkaryl radicals, such as tolyl and dimethylphenyl radicals; and the like. Substituted hydrocarbon radicals include halogenated hydrocarbon radicals, such as chloromethyl, 3-chloropropyl, 3,3,3-trifluoropropyl radicals and the like.

The chlorosilanes having the general formula:

$$Cl_{3-b}SiR_bR'R_bSicl_{3-b}$$

which may be used in the process of the present invention for producing acyloxysilanes include those represented by the formula wherein R may be the same or different substituted or unsubstituted hydrocarbon radicals having from 1 to about 8 carbon atoms. R' is a bivalent hydrocarbon radical, such as, ethylene or phenylene radical; and b is 1 or 2.

The aliphatic carboxylic acids used to produce the acyloxysilanes in the process of the present invention have the formula:

$$R''COOH$$

wherein R'' is an alkyl radical having 1 to about 8 carbon atoms or hydrogen. For example, R'' may include methyl, ethyl, propyl, isopropyl, butyl, isobutyl, pentyl, hexyl, 3-methylpentyl and the like. The aliphatic carboxylic acids used in the process of the invention include formic acid, acetic acid, propionic acid, butyric acid, valeric acid and dimethyl acetic acid. The aliphatic carboxylic acid must be vaporizable since the carboxylic acid is vaporized and passes upward in the vapor phase in the column. The preferred carboxylic acids are those monocarboxylic acids which are lower boiling, and the most preferred carboxylic acid is acetic acid because of its lower boiling point. The boiling points of the aliphatic carboxylic acids increase with increasing molecular weight, and increased temperatures in the reboiler would cause an increase in dimer production. Thus, although many aliphatic carboxylic acids may be used to produce the acyloxysilanes in the process of the present invention, those acids having boiling points which do not promote excessive dimer formation, are preferred. In preferred embodiments, the aliphatic carboxylic acid is vaporized before it is introduced into the column where it passes upward in the vapor phase from a region at or near the bottom of the column countercurrent to the flow of chlorosilane passing downward in the column. Any suitable means by be used for vaporizing the aliphatic carboxyblic acid prior to feeding the aliphatic carboxylic acid vapor into the column. For example, the aliphatic carboxylic acid may be fed to a heat exchanger at a controlled rate; the carboxylic acid is then vaporized in the heat exchanger; and the aliphatic carboxylic acid vapor is then fed into the base or bottom of the column. Any suitable device may be used to regulate the addition of the aliphatic carboxylic acid into the heat exchanger, into the reboiler, and/or into the column. In other embodiments, liquid aliphatic carboxylic acid may be fed into the reboiler or the column or both, or both liquid and vapor aliphatic carboxylic acid may be fed into the reboiler or the column or both. It is also possible to use mixtures of aliphatic carboxylic acids in the process of the present invention.

In the process for producing acyloxysilanes in accordance with the process of the present invention, the improvement comprises introducing the carboxylic acid into the column at such a rate that the carboxylic acid exceeds 1.3 moles per gram atom of silicon-bonded chlorine in the column. Column capacity is increased by as much as 14 to 20 times by a combination of introducing the carboxylic acid into the column at a rate wherein the carboxylic acid exceeds 1.3 moles per gram atom of silicon-bonded chlorine in the column, operating the column at substantially atmospheric pressure (about 760 mm. Hg pressure) and removing low boiling impurities. Thus, in accordance with the process of the present invention, the introduction of a substantial excess of aliphatic carboxylic acid into the column is critical, and as used herein, a substantial excess of aliphatic carboxylic acid is that amount which exceeds 1.3 moles per gram atom of silicon-bonded chlorine in the column, the silicon-bonded chlorine being the chlorine content of the chlorosilane passing downward in the column and flowing countercurrent to the aliphatic carboxylic acid in the vapor phase passing upward in the column.

In preferred embodiments, the aliphatic carboxylic acid is introduced into the column at such a rate that the ratio of carboxylic acid to chlorosilane is between about 1.35 and about 2.1 gram moles of carboxylic acid per gram atom of silicon-bonded chlorine. In one of the most preferred embodiments, the amount of aliphatic carboxylic acid introduced into the column is introduced at such a rate that the ratio of carboxylic acid to chlorosilane is about 1.6 to about 1.7 gram moles of aliphatic carboxylic acid per gram atom of silicon-bonded chlorine. When the amount of aliphatic carboxylic acid exceeds 1.3 moles per gram atom of silicon-bonded chlorine in the column, operated at atmospheric pressure, and when low boiling impurities (by-products) are removed from the column, there is an excess of aliphatic carboxylic acid in the column and reaction conditions are sufficient to cause a more rapid reaction of the carboxylic acid with the chlorosilane, and there is an increase in column capacity of about 14 to about 20 times over those embodiments wherein the aliphatic carboxylic acid/chlorosilane ratio is less than about 1.3 mole per gram atom of silicon-bonded chlorine in the column.

In accordance with the invention, the process for producing acyloxysilanes is carried out in a packed column equipped with a reboiler, overhead condenser and, optionally, a heat exchanger for vaporizing the carboxylic acid. Generally, the column used for the process of the invention is not critical and may be any packed column which can also be used for fractionation distillations. Low boiling reaction products and contaminants are distilled and are collected after they are condensed in the overhead condenser. The removal of the low boiling contaminants and reaction by-products maintains column temperatures at a maximum.

The aliphatic carboxylic acid is fed into the column at or near the base of the column. The chlorosilane is fed to the column at a controlled rate at a point sufficiently below the top of the column to permit a partial reaction of the chlorosilane and the aliphatic carboxylic acid, for example, at least one of the chlorines of the chlorosilane reacts with the aliphatic carboxylic acid. Heat is applied to the reboiler to control the boil-up rate of the column and the pressure drop across the column. A small amount of condensate reflux from the overhead condenser is removed at the top of the column to eliminate low boiling impurities that would otherwise lower the temperature in the column. By-product hydrogen chloride gas escapes from the overhead condenser to suitable recovery or disposal equipment.

The acyloxysilane product forms in the packed column as a result of the reaction between the chlorosilane passing downward in the column and aliphatic carboxylic acid vapor passing countercurrent thereto in an upper direction in the column. The acyloxysilane product passes down the column to the reboiler, and a solution of acyloxysilane in aliphatic carboxylic acid can be continuously or intermittently drawn from the reboiler. Subsequent distillation of the solution of carboxylic acid and acyloxysilane generally provides an acyloxysilane containing less than 10.5 ppm. chloride (the sum of unreacted chlorosilane and hydrogen chloride).

The reactant flow pattern in the reaction column is a countercurrent flow of aliphatic carboxylic acid and the chlorosilane in order to drive the reversible reaction to completion. That is, the aliphatic carboxylic acid reactant is introduced to the base of the column or the reboiler and moves upward as a vapor of the aliphatic carboxylic acid while chlorosilane and partly acyloxylated silanes move down the column in the liquid phase. The chlorosilane, for example, methyltrichlorosilane, reactant first passes in an upward direction in the column because of its lower boiling point and continues in its passage upward in the column until one of the chlorines in the chlorosilane has reacted with the aliphatic carboxylic acid to increase the boiling point of the monomer at which point the movement of the material in the column is reversed, and it begins a downward passage in the column. It is for this reason that the chlorosilane is fed to the column at a point sufficiently below the top of the column to allow partial reaction of the chlorosilane with the carboxylic acid vapor in the column while the chlorosilane monomer is passing upward in the column. The position of the chlorosilane feed stream can be easily adjusted to obtain optimum reaction conditions for the particular distillation column and other equipment used to carry out the process. Although it is not critical, generally the flow pattern of the reactants in the reaction column is countercurrent below the chlorosilane feed point, and the flow pattern is both countercurrent and co-current above the chlorosilane feed point in the column. One skilled in the art can provide various combinations of and locations of feed streams to carry out the process of the present invention without undue experimentation.

Although the length of the column is generally not critical, the height of the column must be of sufficient length for the reaction of the chlorosilane and carboxylic acid. The length of the column is influenced by several factors including: (1) the temperature in the column, (2) the ratio of carboxylic acid to chlorosilane, (3) the boil-up rate in the column, (4) the feed rate of chlorosilane and carboxylic acid, (5) the size and type of packing used in the column, and (6) the flow pattern of carboxylic acid and chlorosilane in the column. Minimum length and diameter of the column result in improved economics, and accordingly, it is desirable to minimize the length and diameter of the column required to process chlorosilane at a given rate of production. In accordance with the process of the present invention, this has been realized by improvements in the foregoing factors and especially in factors 1, 2, 3 and 6 and combinations thereof.

In preferred embodiments, the column is packed with suitable packing. Most conventional corrosion resistant packing materials may be used. One type of preferred packing material is a chemical porcelain material known as Intalox saddles. Other packing materials include Raschig rings and glass helices.

In the process of the present invention for producing acyloxysilanes, the reaction of the chlorosilane with aliphatic carboxylic acid may be carried out at any suitable pressure. In preferred embodiments, the reaction is carried out at atmospheric pressure, that is at about 760 mm Hg. However, the process may also be carried out in accordance with the present invention by reducing the pressure below atmospheric pressure, and in such cases the reaction is carried at at pressures between about 10 mm Hg. and about 760 mm Hg. Pressures below atmospheric can be used, but they are not preferred because column temperature will be reduced accordingly, and the rate of reaction between the chlorosilane and carboxylic acid will be reduced. This must be compensated for by an increase in column length and/or a reduction in the through-put rate. It is also possible to carry out the process of this invention at pressures greater than atmospheric pressure, however, increased reboiler temperatures are generally required at elevated pressures. Pressures above atmospheric will also require increased column temperatures resulting in increased rate of reaction, reduced column length and/or increased allowable throughput rate, however, the higher reboiler temperature will result in increased rate of dimer formation. Thus, in certain cases, the use of increased pressure is not practical if dimer formation occurs at a significant rate.

The solutions in the column and the reboiler are generally maintained at their boiling point, that is, the column must be operated as a distillation column. Acyloxysilanes have high boiling points, for example, methyltriacetoxysilane boils at 220° C. at 760 mm Hg., and acyloxysilanes usually decompose at temperatures below their atmospheric boiling points. As explained above, boiling of the solutions in the column and the reboiler at practical and tolerable temperatures can be affected by reducing the absolute pressure. Furthermore, the boiling can be affected by introducing a lower boiling material, such as a solvent. In the process of the present invention, the aliphatic carboxylic acid in excess of the chlorosilane reactant act as a solvent so that the reacting mixture and products formed therefrom are a solution of the silane monomer and the product in the aliphatic carboxylic acid, such as acetic acid. Thus, the product is discharged from the reboiler as a solution of the acyloxysilane in aliphatic carboxylic acid. The amount of excess aliphatic carboxylic acid over the chlorosilane reactant in the column feed stream determines the composition and boiling point of the solution in the reboiler, and consequently, determines the rate of formation of undesirable dimer in the reboiler.

Generally, the chlorosilane is reacted with the aliphatic carboxylic acid at a temperature which corresponds or substantially corresponds to the boiling point of the carboxylic acid used under prevailing conditions of pressure in the column. In preferred embodiments, the temperature of the column is maintained between about 95° C. to about 125° C. Furthermore, in preferred embodiments, the temperature in the column is maintained in gradients throughout the column, the temperature at the top of the column being lower than the temperature at the bottom of the column. Under one set of preferred reaction conditions, the temperature is maintained at reaction gradients throughout the column, the temperature at the top of the column being the lowest temperature and maintained at about 95° C. to about 100° C., and the temperature at the bottom of the column being the higher temperature and maintained at about 120° C. to about 125° C. Generally, the temperatures in the column are not controlled directly. A particular temperature depends upon the particular ingredients, such as the acid and the silane, and the pressure used in the system.

For economic reasons and in preferred embodiments, the process for the production of acyloxysilanes in general, and more specifically, for the production of methyltriacetoxysilane from the reaction of methyltrichlorosilane and acetic acid, is carried out as a continuous process wherein the acid vapor is continuously fed into the lower end of a vertical packed column and a stream of chlorosilane is continuously fed into the column and passed downward therein, wherein hydrogen chloride gas, acetic acid and low boiling reaction products are removed from the top of the distillation column. The acyloxysilane and unreacted acid are collected at the bottom of the column in a collecting vessel or reboiler and removed continuously therefrom. The acyloxysilane may then be separated from the acid by any suitable means, such as by distillation.

The following specific examples describe the process of this invention. They are intended for illustrative purposes only and should not be construed as limiting the present invention.

EXAMPLE 1

A glass column having a 7.6 cm (3 inch) internal diameter was constructed of nine 30.5 cm (12 inch) lengths of glass pipe alternated with nine 7.6 cm×38.1 cm (3 inch×15 inch) glass reducing crosses. Four packing support plates of single bubble cap design supported the column packing material which, in the case of this example, was 0.95 cm (3/8 inch) chemical porcelain saddles, to provide a total of 432.8 cm (14.2 feet) of packing material in the glass column. The porcelain, chemical stoneware tower filling materials used in this example were Intalox saddles (Intalox is a trademark of U.S. Stoneware Company). Additional 7.6 cm×3.8 cm reducing crosses were installed at the base of the column and at the top of the column without packing material.

The side flanges of the reducing crosses were equipped with thermal wells containing thermocouples, devices for sampling liquids at that point of the column, and feed tubes as desired to provide a temperature profile of the column, samples of the liquid in the column every 55.8 cm (22 inches), and flexibility of reactant feed points respectively. The column was jacketed, and the jacket was heated with electrical resistance heating tape to minimize heat loss from the column. Thermocouples in the annular jacket space indicated the jacket temperature. The jacket was suitably insulated to prevent heat loss.

A reboiler installed below the column was a 20 liter glass flask heated with an electrical mantel and equipped with a thermal well containing a thermocouple, a 7.6 cm (3 inch) top flange connecting the flask to the column and a top flange for pressure measurement. The reboiler flask was equipped with a bottom outlet for discharge of the product, and adjustable overflow pipe to control the liquid level in the reboiler flask. A collection flask was provided to collect the product from the reboiler flask, and the collection flask was equipped with a pressure equallizing line to the reboiler so that the collection flask could be held at the same pressure as the reboiler flask.

The top of the column was equipped with a reflux splitter, a water-cooled condenser and a brine-cooled condenser for cooling to −10° C. The uppermost part of the column was the brine-cooled condenser, and hydrogen chloride gas was removed from the brine cooled condenser by means of a pipe to a disposal system which provided for free venting of the column to atmospheric pressure. The column was equipped with auxillary equipment including a pump for feeding chlorosilane reactant at a variable controlled rate through a feed tube located 161.54 cm (5.3 feet) below the top of the packing with the tube discharging to the center of the 7.6 cm raction column. A second variable controlled rate pump was provided to feed the aliphatic carboxylic acid through an oil heated heat exchanger where the aliphatic carboxylic acid was vaporized so that the acid could be fed to the base of the column in vapor form. Multiple temperature measurement means, column pressure drop measurement means and means for measuring the feed of reactants and collection of product were also provided.

For the preparation of methyltriacetoxysilane, 9.07 kg (20 lbs.) of a solution containing about 50% acetic acid, 45% methyltriacetoxysilane, 1% acetic anhydride, and 3.4% dimethyltetracetoxydisiloxane were charged to the reboiler flask of the reaction column described above. Heat was applied to the reboiler and boil-up established in the column at a column pressure drop of 4 inches of water. Methyltrichlorosilane and acetic acid feeds were initiated into the column. Methyltrichlorosilane at room temperature was fed at a nominal rate of 3.63 Kg (8 lbs.)/hour at a point 161.54 cm (5.3 feet) below the top of the chemical porcelain stoneware packing material in the column. Acetic acid was fed at a nominal rate of 7.25 Kg (16 lbs)/hour, a 66% stoichiometric excess, through the heat exchanger to vaporize the acetic acid. The acetic acid vapors were then introduced to the base of the glass column at a point immediately below the chemical porcelain stoneware column packing material. The heat input at the reboiler was adjusted to provide a column pressure drop of 14 to 15 inches of water. The reflux splitter was set to give an 80/1 reflux ratio on the condensate returning from the overhead condensers. Nine hours after initiation of reactant feeds, samples of down-coming liquid were taken from 8 points in the column and from the reboiler discharge. These samples were analyzed for ionic chloride content. An identical set of samples were taken 10 hours after initiation of feeds and analyzed for ionic chloride content.

The column temperatures and ionic chloride concentrations at 9 hours and at 10 hours are set forth in Table 1 below where the sample point is the distance below the top of the chemical porcelain stoneware column packing material, and percentages of ionic chloride were determined by the method set forth below.

The overhead distillate rate was determined to be 0.15 Kg (0.33 lbs.)/hour, and the product collection rate was measured at 9.03 Kg (17.7 lbs.)/hour.

An approximate analysis of the overhead distillate composition was as follows:

| Acetyl Chloride: | 0.3% |
|---|---|
| Methyltrichlorosilane: | 1.3% |
| Acetic Acid: | 90.0% |
| $C_6H_{12}$Olefins (2 isomers): | 1.8% |
| Hydrogen Chloride: | 3.5% |

The composition of the product collected from the reboiler in the product collection flask was:

| Acetic Acid: | 49.3% |
|---|---|
| Acetic Anhydride: | 0.9% |
| Methyltriacetoxysilane: | 46.2% |
| Dimethyltetraacetoxydisiloxane: | 3.2% |
| Ionic Chloride: | <1ppm |

The amounts of the measured ingredients in the overhead distillate and the end product reported above were measured as percent area of the gas chromatographic curve.

The ionic chloride concentration of samples was determined by dissolving a weighed amount of sample in a mixture of 95% by volume acetone and 5% by volume water and performing a potentiometric titration with a standardized solution of silver nitrate dissolved in methanol.

TABLE 1

IONIC CHLORIDE AND TEMPERATURE MEASUREMENTS AT VARIOUS POINTS IN THE SYSTEM FOR THE PRODUCTION OF METHYLTRIACETOXYSILANE

| SAMPLE* POINT (cm.) | TEMPERATURE °C. | IONIC CHLORIDE 9 HOURS | CONCENTRATION 10 HOURS |
|---|---|---|---|
| CONDENSER | 98 | — | — |
| 12.2 | 105 | — | — |
| 70.1 | 110 | — | — |
| 106.7 | 114 | 9.5% | 8.2% |
| 161.5 | 120 | 14.4% | 17.7% |
| 213.4 | 122 | 640ppm | 890ppm |
| 256.0 | 122 | 88ppm | 29ppm |
| 313.9 | 122 | <1ppm | <1ppm |
| 350.5 | 122 | <1ppm | <1ppm |
| 405.4 | 122 | <1ppm | <1ppm |
| 432.8 | — | <1ppm | <1ppm |
| REBOILER | 139 | <1ppm | <1ppm |

*Sample Point is measured in centimeters from the top of the packing material in the column.

It can be seen from the data in Table 1 that the reaction of the chlorosilane and acetic acid was completed at a column length between 256 cm and 313.9 cm as measured from the top of the packing material in the column. As seen from the data of Example 1, the methyltriacetoxysilane was 46.2% of the product composition in 49.3% acetic acid. The amount of excess acetic acid over the chlorosilane in the column determines the composition and boiling point of the solution in the reboiler flask and consequently, the rate of formation of dimer impurity in the reboiler.

EXAMPLE 2

Various amounts of acetic acid in excess of the trichloromethylsilane were used in the apparatus of Example 1 to determine the ratio of dimer impurity formed relative to the methyltriacetoxysilane measured in the product. All other conditions and parameters are identical to those disclosed in Example 1 except for the molar ratio of acetic acid to the molar ratio of trichloromethylsilane. The following data for the preparation of methyltriacetoxysilane in the reaction column having a flask as a reboiler relates the dimer content of methyltriacetoxysilane to the stoichiometric ratio of acetic acid to methyltrichlorosilane:

| Mols Acetic Acid per Mol $CH_3SiCl_3$ | Ratio gm-mols $CH_3COOH$ to gm-atoms SiCl | Ratio of Dimer to methyltriacetoxy silane in Product |
|---|---|---|
| 3.60 | 1.20 | 0.11 |
| 3.99 | 1.33 | 0.09 |
| 4.41 | 1.47 | 0.07 |
| 4.98 | 1.66 | 0.044 |
| 6.24 | 2.08 | 0.038 |

Samples of the downcoming liquid taken at the base of the column will typically have a dimer/monomer ratio of approximately 0.016 when operating at an acetic acid/trichloromethylsilane ratio of 4.98 while the product discharged from the reboiler will have a dimer/monomer ratio of typically 0.044. Clearly the major location of dimer formation is in the reboiler as a result of higher temperatures and residence times in the reboiler. It is believed that the dimer formation is the result of thermal decomposition of the acetoxysilane.

EXAMPLE 3

In a glass column and under conditions identical to those discussed above for Example 1, the methyltrichlorosilane was introduced into the glass column at a point 256.0 cm (8.4 feet) from the top of the column packing material at 3.63 Kg (8.0 lbs.)/hour, and 75% of the acetic acid was introduced to the base of the column in the vapor phase and 25% of the acetic acid was introduced at the top of the column in a liquid form at 65° C. for a total input of 7.25 Kg (16 lbs.)/hour. The column pressure drop was 10.5 inches of water. All other conditions were the same as those disclosed in Example 1 including column height, column diameter, column packing material and the like. The sampling data for the ionic chloride, acetic acid, acetic anhydride, methyltrichlorosilane, dichlorosilane, monochlorosilane, methyltriacetoxysilane and dimer were taken at various column heights. The data is recorded in Table 2 below where, except as otherwise indicated, all data is recorded in percentages (based upon the area of the curve in gas chromatographic analysis).

TABLE 2

MEASUREMENTS AND SAMPLING DATA AT VARIOUS POINTS IN THE SYSTEM FOR THE PRODUCTION OF METHYLTRIACETOXYSILANE

| SAMPLE POINT (cm) | TEMP. °C. | CHLORIDE (p.p.m.) | ACETIC ACID | ACETIC ANHYDRIDE | MeSiCl$_3$[1] | SiCl$_2$ | SiCl | MTAS[2] | DIMER |
|---|---|---|---|---|---|---|---|---|---|
| CONDENSER | 89 | — | — | — | — | — | — | — | — |
| 12.2 | 100 | — | — | — | — | — | — | — | — |
| 70.1 | 106 | — | — | — | — | — | — | — | — |
| 106.7 | 108 | 5.4 | 92% | 0.2% | 1.4% | 0.01% | 0 | 2% | 0.2% |
| 161.5 | 109 | 2.3 | 95% | 0.2% | 0.1% | TRACE | 0 | 3% | 0.5% |
| 213.4 | 114 | 3.2 | 84% | 0.1% | 0.2% | TRACE | 0 | 11.3% | 0.7% |
| 256.0 | 119 | 3.7 | 80% | 0.1% | 0.5% | 0.05% | 0 | 14.4% | 0.7% |
| 313.9 | 122 | 72.0 | — | 0.2% | 0 | 0 | 0 | — | — |
| 350.5 | 123 | 9.0 | 89% | 0.2% | 0 | 0 | 0 | 9.8% | 0.3% |
| 405.4 | 123 | 5.0 | 89% | 0.4% | 0 | 0 | 0 | 9.8% | 0.3% |
| 432.8 | — | 2.0 | 88% | 0.7% | 0 | 0 | 0 | 10.8% | 0.4% |
| REBOILER | 140 | 3.0 | 45% | 1.0% | 0 | 0 | 0 | 50.0% | 3.4% |

[1]Methyltrichlorosilane
[2]Methyltriacetoxysilane
SiCl$_2$ = CH$_3$Si(OOCCH$_3$)Cl$_2$
SiCl = CH$_3$Si(OOCCH$_3$)$_2$Cl The overhead distillate in Example 3 had a methyltrichlorosilane content of about 2 to about 2.5%. It can be seen from the data in Table 2 that although the acetic acid was introduced at two different areas in the column, acceptable concentrations of the methyltriacetoxysilane product dissolved in acetic acid was obtained by the process of the present invention. Thus, although the acetic acid is fed at or near the bottom of the column in the vapor phase, it is possible to complement the excess acetic acid fed into the column by introducing liquid acetic acid into other regions of the column including the top of the column. In Example 3, 25% of the acetic acid was introduced into the top of the column in a liquid phase and 75% of the acetic acid was introduced into the bottom of the column in the vapor phase.

In accordance with at least some of the objects of the invention, acyloxysilanes have been prepared by reacting a chlorosilane with an aliphatic carboxylic acid in a column at an elevated temperature by introducing the carboxylic acid into the column at such a rate that the carboxylic acid exceeds 1.3 mole per gram atom of silicon-bonded chlorine in the column. In at least portions of the column, the aliphatic carboxylic acid in the vapor phase passes upward from the bottom of the column countercurrent to the flow of the chlorosilane passing downward from the top of the column. Low boiling reaction by-products are removed from the top of the column while the acyloxysilane product dissolved in acetic acid is accumulated at the bottom of the column.

When compared to the prior art processes which introduce carboxylic acid into the column in amounts less than 1.3 mole per gram atom of silicon-bonded chlorine in the column and operate at absolute pressures substantially below atmospheric pressure, the process of the present invention permits a 14 to 20 fold increase in column capacity over the processes of the prior art. The larger capacity of the process of the present invention results from higher column temperatures, greater vapor density and increased liquid loading in a reaction column operated at atmospheric pressure.

While the invention has been described with respect to preferred embodiments, it will be apparent that certain modifications and changes can be made without departing from the spirit and scope of the invention, and therefore, it is intended that the foregoing disclosure be limited only by the claims appended hereto.

What is claimed is:

1. In a process for producing acyloxysilane by reacting a chlorosilane with an aliphatic carboxylic acid in a column at an elevated temperature wherein the aliphatic carboxylic acid in the vapor phase passes upward from the bottom of the column countercurrent to the flow of the chlorosilane passing downward in the column, the improvement comprising introducing the carboxylic acid into the column at such a rate that the carboxylic acid exceeds 1.3 mole per gram atom of silicon-bonded chlorine in the column and removing low boiling reaction by-products from the top of the column while collecting the acyloxysilane product at the bottom of the column.

2. The process of claim 1 wherein the carboxylic acid is introduced into the column at such a rate that the ratio of carboxylic acid to chlorosilane is between about 1.35 and about 2.1 gram moles of carboxylic acid per gram atom of silicon-bonded chlorine.

3. The process of claim 1 wherein the carboxylic acid is introduced into the column at such a rate that the ratio of carboxylic acid to chlorosilane is about 1.6 to about 1.7 gram moles of carboxylic acid per gram atom of silicon-bonded chlorine.

4. The process of claim 1 further comprising operating the column at about 760 mm Hg pressure.

5. The process of claim 1 further comprising maintaining the temperature of the column between about 95° C. to about 125° C.

6. The process of claim 1 or 5 wherein the temperature is maintained in gradients throughout the column, the temperature at the top of the column being lower than the temperature at the bottom of the column.

7. The process of claim 1 or 5 wherein the temperature is maintained in gradients throughout the column, the temperature at the top of the column being about 95° C. to about 100° C. and the temperature at the bottom of the column being about 120° C. to about 125° C.

8. The process of claim 1 further comprising heating the aliphatic carboxylic acid to vaporize the acid and feeding the aliphatic carboxylic acid vapor into the column.

9. The process of claim 1 comprising continuously passing the aliphatic carboxylic acid in the vapor phase upward from the bottom of the column countercurrent to the continuous flow of chlorosilane passing downward in the column.

10. The process of claim 1 further comprising distilling the acyloxysilane product to remove unreacted aliphatic carboxylic acid and by-products therefrom.

11. The process of claim 1, 2, 3 or 4 wherein the carboxylic acid is acetic acid.

12. A process for the continuous production of methyltriacetoxysilane from the reaction of methyltrichlorosilane and acetic acid, comprising:
 (a) feeding continuously a vapor of acetic acid into the lower end of a substantially vertical packed column so that the acetic acid vapor passes upward in the column at a rate wherein the acetic acid exceeds 1.3 moles per gram atom of silicon-bonded chlorine in the column;
 (b) passing a stream of methyltrichlorosilane downward in the heated column countercurrent to the flow of acetic acid vapor;
 (c) removing hydrogen chloride, acetic acid and low boiling reaction products from the top of the column; and
 (d) collecting and continuously removing the methyltriacetoxysilane, unreacted acetic acid and reaction by-products from a collection vessel at the bottom of the column, the collecting vessel being maintained at a temperature higher than the temperature of the column.

13. The process of claim 12 wherein the acetic acid is introduced into the column at such a rate that the acetic acid to methyltrichlorosilane is about 1.6 to about 1.7 gram moles of acetic acid per gram atom of silicon-bonded chlorine.

14. The process of claim 12 further comprising operating the column at about 760 mm Hg. pressure.

15. The process of claim 12 further comprising maintaining the temperature of the column between about 95° C. to about 125° C.

16. The process of claim 12 or 15 wherein the temperature is maintained in gradients throughout the column, the temperature at the top of the column being lower than the temperature at the bottom of the column.

17. The process of claim 12 or 15 wherein the temperature is maintained in gradients throughout the column, the temperature at the top of the column being about 95° C. to about 100° C. and the temperature at the bottom of the column being about 120° C. to about 125° C.

18. The process of claim 12 further comprising distilling the methyltriacetoxysilane to remove unreacted acetic acid and reaction by-products therefrom.

* * * * *